US006551251B2

(12) United States Patent
Zuckerwar et al.

(10) Patent No.: US 6,551,251 B2
(45) Date of Patent: Apr. 22, 2003

(54) PASSIVE FETAL HEART MONITORING SYSTEM

(75) Inventors: Allan J. Zuckerwar, Williamsburg, VA (US); Dennis L. Mowrey, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/784,413

(22) Filed: Feb. 13, 2001

(65) Prior Publication Data

US 2002/0068874 A1 Jun. 6, 2002

Related U.S. Application Data

(60) Provisional application No. 60/182,343, filed on Feb. 14, 2000.

(51) Int. Cl.[7] .......................... A61B 7/00; A61B 5/0444
(52) U.S. Cl. ..................... 600/528; 600/511
(58) Field of Search ................. 128/901, 920; 600/508, 511, 528, 586, 376, 522; 607/902

(56) References Cited

U.S. PATENT DOCUMENTS

| 4,122,843 A | 10/1978 | Zdrojkowski | |
|---|---|---|---|
| 4,299,234 A | 11/1981 | Epstein et al. | |
| 4,398,116 A | 8/1983 | Lewis | |
| 4,672,976 A | 6/1987 | Kroll | |
| 4,781,200 A | * 11/1988 | Baker | 600/483 |
| 4,920,966 A | 5/1990 | Hon et al. | |
| 5,140,992 A | * 8/1992 | Zuckerwar et al. | 600/528 |
| 5,209,237 A | * 5/1993 | Rosenthal | 367/45 |
| 5,492,129 A | 2/1996 | Greenberger | |
| 5,524,631 A | 6/1996 | Zahorian et al. | |
| 6,245,025 B1 | 6/2001 | Torok et al. | |

FOREIGN PATENT DOCUMENTS

| DE | 41 18359 A1 | 12/1992 |
|---|---|---|
| EP | 0 310 380 A2 | 4/1989 |
| GB | 1 348 154 | 3/1974 |
| WO | WO 95/06525 | 3/1995 |
| WO | WO 98/37807 | 9/1998 |

* cited by examiner

Primary Examiner—Kennedy Schaetzle
Assistant Examiner—Kristen Droesch
(74) Attorney, Agent, or Firm—Helen M. Galus

(57) ABSTRACT

A fetal heart monitoring system and method for detecting and processing acoustic fetal heart signals transmitted by different signal transmission modes. One signal transmission mode, the direct-contact mode, occurs in a first frequency band when the fetus is in direct contact with the maternal abdominal wall. Another signal transmission mode, the fluid propagation mode, occurs in a second frequency band when the fetus is in a recessed position with no direct contact with the maternal abdominal wall. The second frequency band is relatively higher than the first frequency band. The fetal heart monitoring system and method detect and process acoustic fetal heart signals that are in the first frequency band and in the second frequency band.

31 Claims, 5 Drawing Sheets

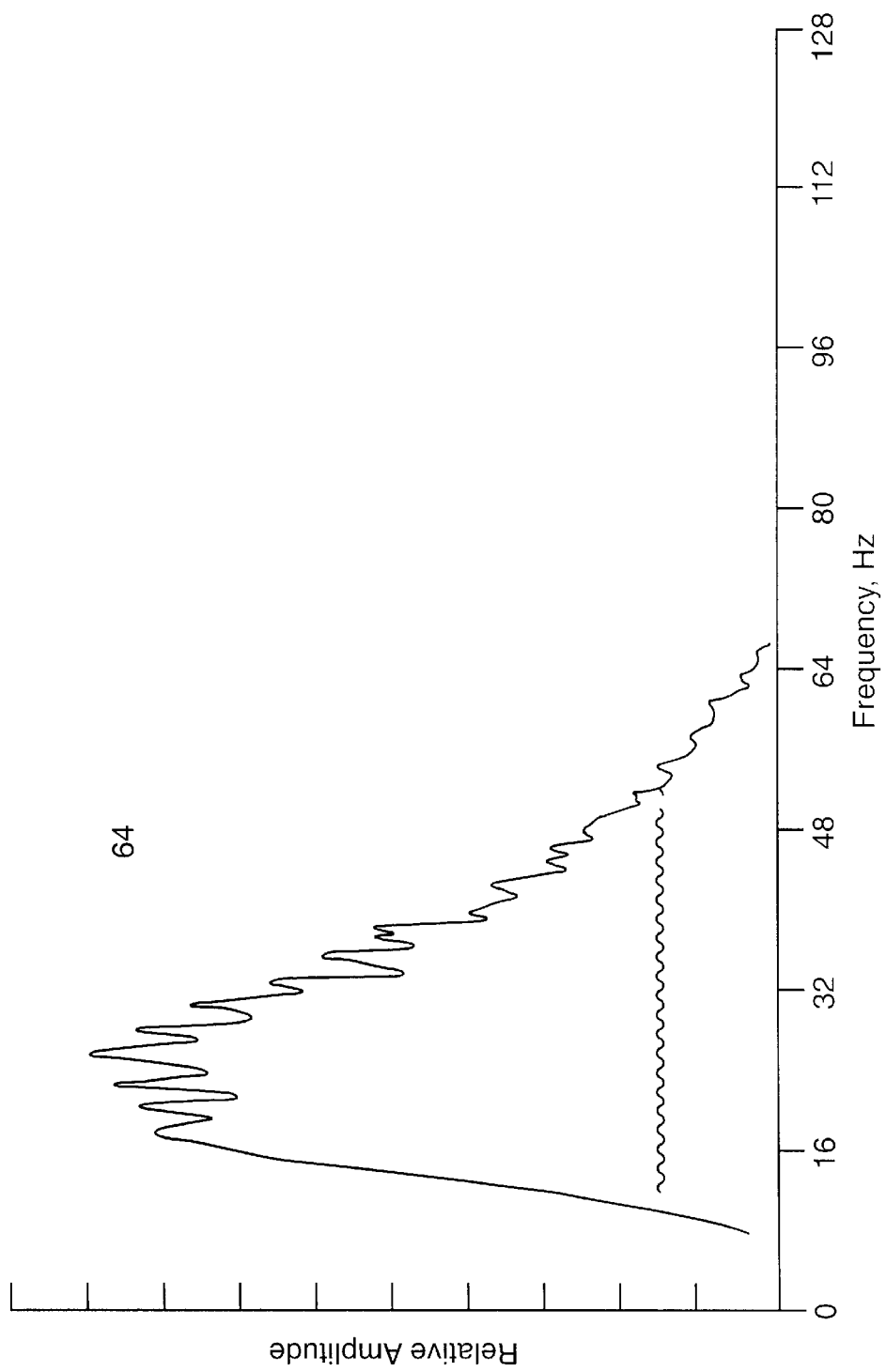

PASSIVE FETAL HEART MONITORING SYSTEM

CLAIM OF BENEFIT OF PROVISIONAL APPLICATION

Pursuant to 35 U.S.C. §119, the benefit of priority from provisional application 60/182,343, with a filing date of Feb. 14, 2000, is claimed for this non-provisional application.

ORIGIN OF THE INVENTION

The invention described herein was made by an employee of the United States Government and may be used by or for the Government for governmental purposes without the payment of any royalties thereon or therefor.

BACKGROUND OF THE INVENTION

1. Technical Field of the Invention

The present invention relates broadly to the field of biomedical transducers and more particularly, to a passive sensor monitoring the heart of a fetus.

2. Related Art and Problem to be Solved

Conventional acoustic fetal heart monitors are described in U.S. Pat. Nos. 4,122,843, 4,299,234, 4,672,976, 4,781,200, 5,140,992 and 5,524,631. U.S. Pat. No. 4,781,200 describes an ambulatory non-invasive automatic fetal monitoring system to detect signals in the 50–110 HZ frequency band. U.S. Pat. No. 4,299,234 describes a fetal heart rate apparatus that simultaneously processes both electro-cardiographic and mechanical cardiographic signals, but does not specifically mention a frequency bandwidth. U.S. Pat. No. 4,672,976 describes a heart sound sensor that utilizes a hydrophone assembly to detect signals in the 10 Hz–2 kHz frequency band. U.S. Pat. No. 4,122,843 describes an electrode system for a heart rate monitor but does not specifically mention a frequency bandwidth.

Examination of these aforementioned patents reveals that, although a particular frequency bandwidth may be specified, none of these patents recognize that there are different frequency bands in which acoustic cardiac signals are transmitted, depending upon the position of the fetus with respect to the maternal abdominal wall. For example, the frequency bandwidth specification of 50–110 Hz disclosed in U.S. Pat. No. 4,781,200 completely excludes the 16–32 Hz band which contains the bulk of the fetal heart energy. In another example, U.S. Pat. No. 4,299,234 discloses a specified frequency bandwidth of 10 Hz–2 kHz bandwidth. Such a bandwidth includes signals from all modes of transmission and provides no method of discrimination.

Successful monitoring of fetal heart activity depends upon the capability of a fetal monitoring system to detect and process acoustic signals produced by the fetus' heart no matter how the fetus is positioned with respect to the maternal abdominal surface. Such a capability has not been addressed by prior art or conventional devices, methods and techniques.

What is needed is a fetal heart monitoring system that can detect acoustic signals emanating from the heart of the fetus with regard to the position of the fetus with respect to the maternal abdominal surface. In particular, what is needed is a fetal heart monitoring system that can detect acoustic signals emanating from the heart of the fetus whether or not the fetus is in direct contact with the maternal abdominal wall.

It is therefore an object of the present invention to provide a fetal heart monitoring system that fulfills the aforementioned needs and to address the occasional inefficacy of prior art or conventional devices.

Other objects and advantages of the present invention will in part be obvious and will in part be apparent from the specification.

SUMMARY OF THE INVENTION

The above and other objects and advantages, which will be apparent to one of skill in the art, are achieved in the present invention which is directed to a fetal heart monitoring system for detecting and processing acoustic fetal heart signals transmitted by different signal transmission modes. One signal transmission mode, the direct-contact mode, occurs in a first frequency band when the fetus is in direct contact with the maternal abdominal wall. Another signal transmission mode, the fluid propagation mode, occurs in a second frequency band when the fetus is in a recessed position with no direct contact with the maternal abdominal wall. The second frequency band is relatively higher than the first frequency band. The fetal heart monitoring system of the present invention detects and processes acoustic fetal heart signals that are in the first frequency band and second frequency band.

Accordingly, the present invention is directed to, in one aspect, a fetal heart monitoring system, comprising a passive fetal heart monitoring sensor having a plurality of sensor elements for acquiring acoustic signals emitted from a fetus inside a body and outputting a plurality of sensor signals, a selection circuit for selecting a particular one of the sensor signals, a signal processing device having a first signal processing channel for processing acoustic signals in a first frequency band and a second signal processing channel for processing acoustic signals in a second frequency band. The signal processing device has a first state such that the signal processing device outputs sensor signals processed by the first signal processing channel and a second state such that the signal processing device outputs sensor signals processed by the second signal processing channel. The fetal heart monitoring system further includes a monitoring device responsive to the signal processing device for monitoring the characteristics of the processed signals outputted by the signal processing device and determining if such characteristics meet or exceed predetermined criteria, and a control device for configuring the signal processing device to the first state so as to process selected sensor signals with the first signal processing channel if such processed signals meet or exceed the predetermined criteria and for configuring the signal processing device to the second state so as to process selected sensor signals with the second signal processing channel if the sensor signals processed by the first signal processing channel do not meet the predetermined criteria.

The control device configures the signal processing device back to the first state so as to process selected sensor signals with the first signal processing channel if the signals processed by the second signal processing channel do not meet predetermined criteria.

In another aspect of the present invention, the monitoring device can include additional signal filtering capability.

In another aspect, the present invention is directed to a method of monitoring fetal heart activity, comprising the steps of (a) providing a fetal heart monitoring system comprising a passive fetal heart monitoring sensor having a plurality of sensor elements for acquiring acoustic signals emitted from a fetus inside a body and outputting a plurality of sensor signals, and a signal processing device having a first signal processing channel for processing acoustic signals in a first frequency band and a second signal processing channel for processing acoustic signals in a second frequency band, the signal processing device having a first state such that the signal processing device processes sensor signals with the first signal processing channel when such processed signals meet predetermined criteria and a second state such that the sensor signals are processed by the second signal processing channel when the processed signals outputted by the first signal processing channel do not meet predetermined criteria, (b) processing the sensor signals with one of the signal processing channels of the signal processing device, (c) monitoring the characteristics of the processed sensor signals to determine if such processed sensor signals meet predetermined criteria, and (d) configuring the signal processing device so as to process the sensor signals with the other signal processing channel if the processed signals do not meet predetermined criteria.

In one aspect of the method, the processing step comprises the steps of configuring the signal processing device in the first state, filtering the selected sensor signals with a low pass anti-aliasing filter, and filtering the previously filtered selected sensor signals with a high pass filter configured to pass only signals having frequencies in the first frequency band.

In another aspect of the method, the processing step comprises the steps of configuring the signal processing device in the second state, filtering the selected sensor signals with a low pass anti-aliasing filter, filtering the previously filtered selected sensor signals with a high pass filter configured to pass only signals having frequencies in the second frequency band, and thereafter, amplifying the filtered signals.

In yet another possible aspect of the method, the step of monitoring the characteristics of the processed sensor signals to determine if such processed sensor signals meet predetermined criteria comprises additional filtering of the processed sensor signals.

BRIEF DESCRIPTION OF THE DRAWINGS

The features of the invention are believed to be novel and the elements characteristic of the invention are set forth with particularity in the appended claims.

The figures are for illustration purposes only and are not drawn to scale. The invention itself, however, both as to organization and method of operation, may best be understood by reference to the detailed description which follows taken in conjunction with the accompanying drawings in which.

DETAILED DESCRIPTION OF THE INVENTION

In describing the preferred embodiments of the present invention, reference will be made herein to FIGS. 1–5 of the drawings in which like numerals refer to like features of the invention.

Figure 1:
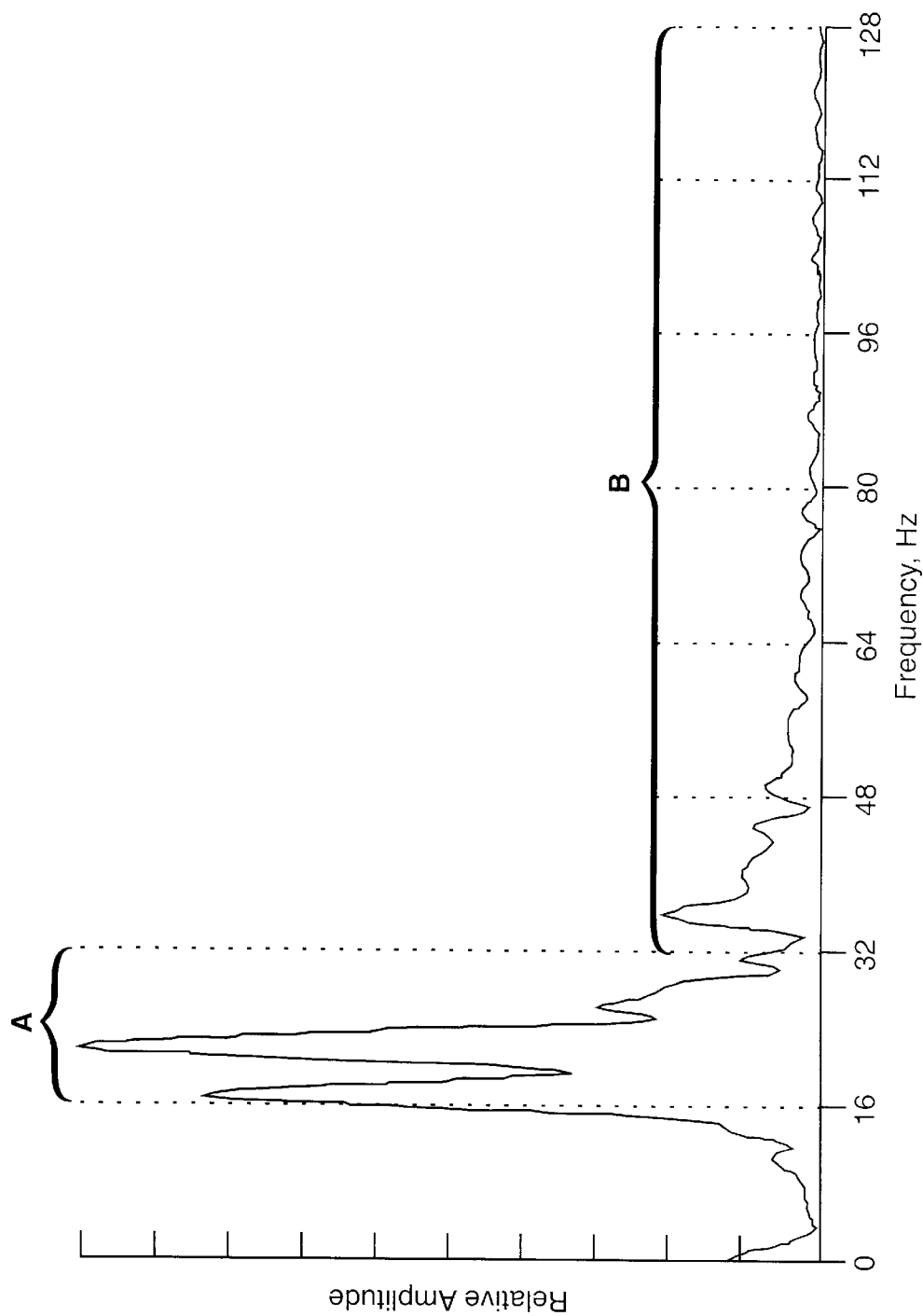
FIG. 1 illustrates the typical frequency spectrum of measured fetal heart sounds.

Referring to FIG. 1, there is shown the typical frequency spectrum of a measured fetal heart sound. The bulk of the fetal acoustic energy lies in the primary frequency band, indicated by the letter A, 16–32 Hz. A secondary frequency band, indicated by letter B, is above 32 Hz. In secondary frequency band B, there is a significantly lower level of fetal energy, the amplitude being typically 30 dB down from the peak amplitude in primary frequency band A. As described in the foregoing discussion, the operation of many conventional fetal heart monitoring systems is based upon the detection of fetal heart signals in primary frequency band A. In accordance with the present invention, primary frequency band A and secondary frequency band B are used in the detection of fetal heart signals.

Figure 2:
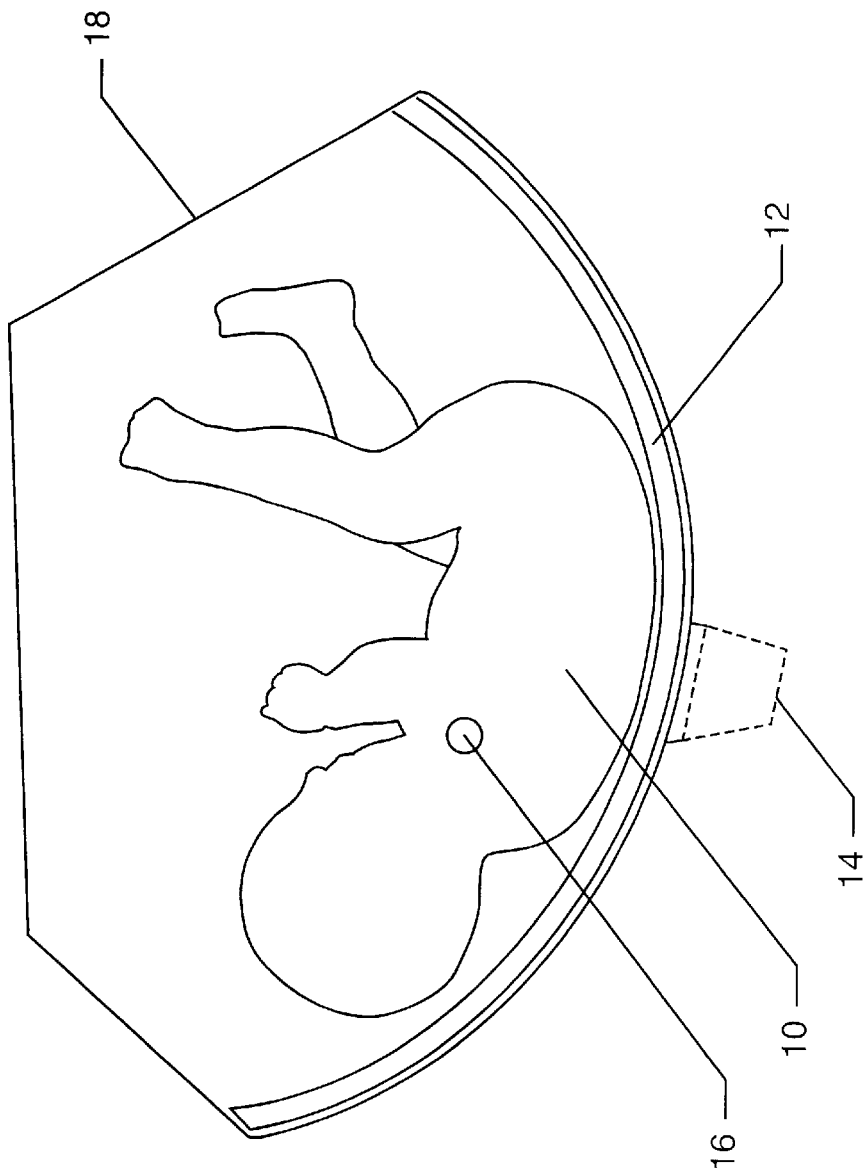
FIG. 2 illustrates a fetus positioned such that its back or shoulders are direct contact with a maternal abdominal wall.
Figure 3:
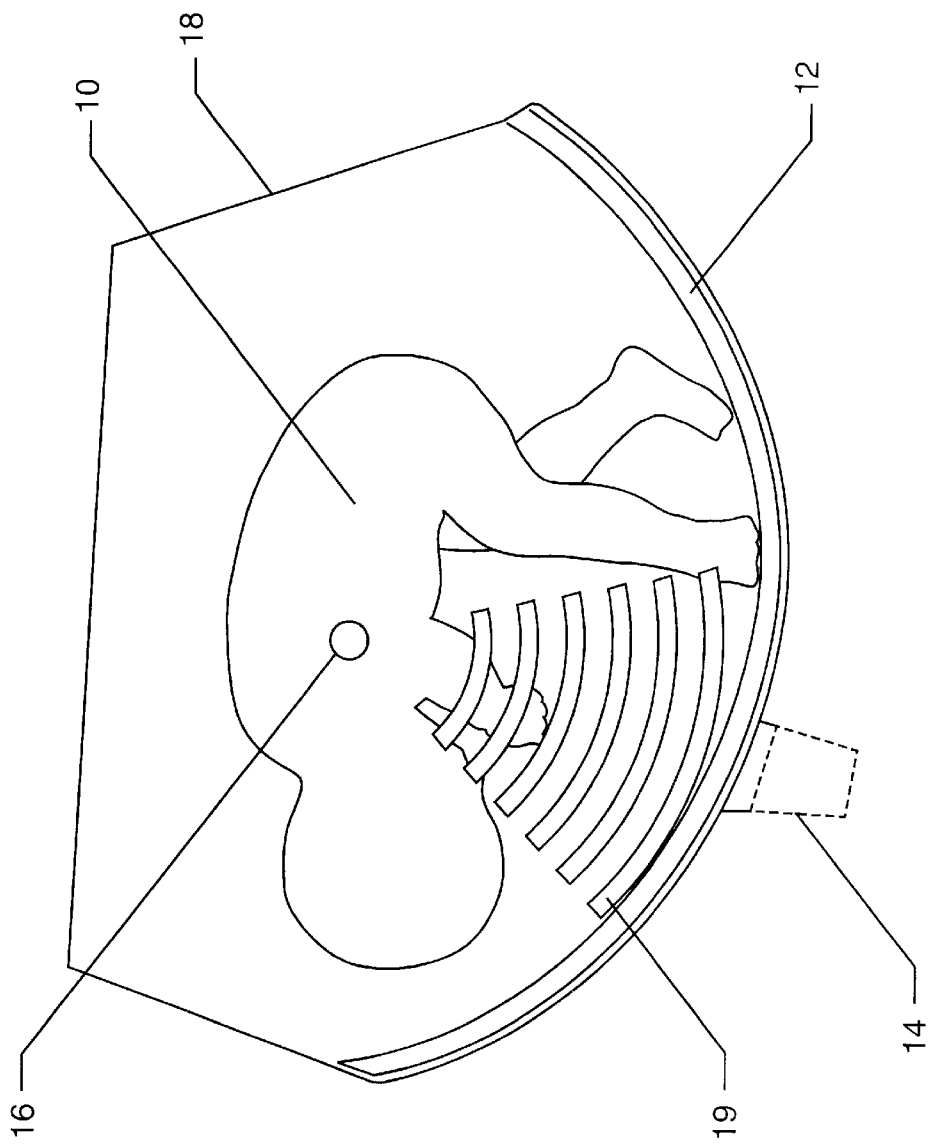
FIG. 3 illustrates a position of a fetus wherein the fetus is turned, facing the maternal abdominal wall.

Referring to FIG. 2, there is shown an illustration of a fetus 10 positioned such that its back or shoulders are in direct contact with maternal abdominal wall 12. Such a position facilitates detection of the fetal heart signals in frequency band A by a known sensor 14 shown in phantom. The opening and closing of the valves in the fetal heart 16 cause the fetus 10 to push against sensor 14, if sensor 14 is located opposite the fetal back or shoulders. This mode of signal transmission is referred to herein as "direct contact" mode. Essentially, no acoustical propagation takes place in the direct contact mode. Referring to FIG. 3, there is shown an illustration of fetus 10 turned or facing abdominal wall 12, but is recessed such that fetus 10 essentially makes no direct contact with the maternal abdominal wall. In such a situation, a body of amniotic fluid 18 is between fetus 10 and sensor 14. Thus, acoustic signals 19 caused by the opening and closing of fetal heart 16 must pass through amniotic fluid 18 in order to reach sensor 14. This mode of signal transmission is referred to herein as "fluid propagation" mode. As a result of the fluid propagation mode, the level and quality of acoustic signals 19 in frequency band A is significantly attenuated and degraded and thereby can prevent successful detection of acoustic signals 19 by sensor 14.

In accordance with the present invention, the fetal heart monitoring system of the present invention reliably and accurately detects acoustic signals emanating from fetal heart 16 whether fetus 10 is positioned as shown in FIG. 2 or as shown in FIG. 3. Specifically, the fetal heart monitoring system of the present invention detects acoustic signals emanating from the fetal heart in both direct contact and fluid propagation modes.

Figure 5:
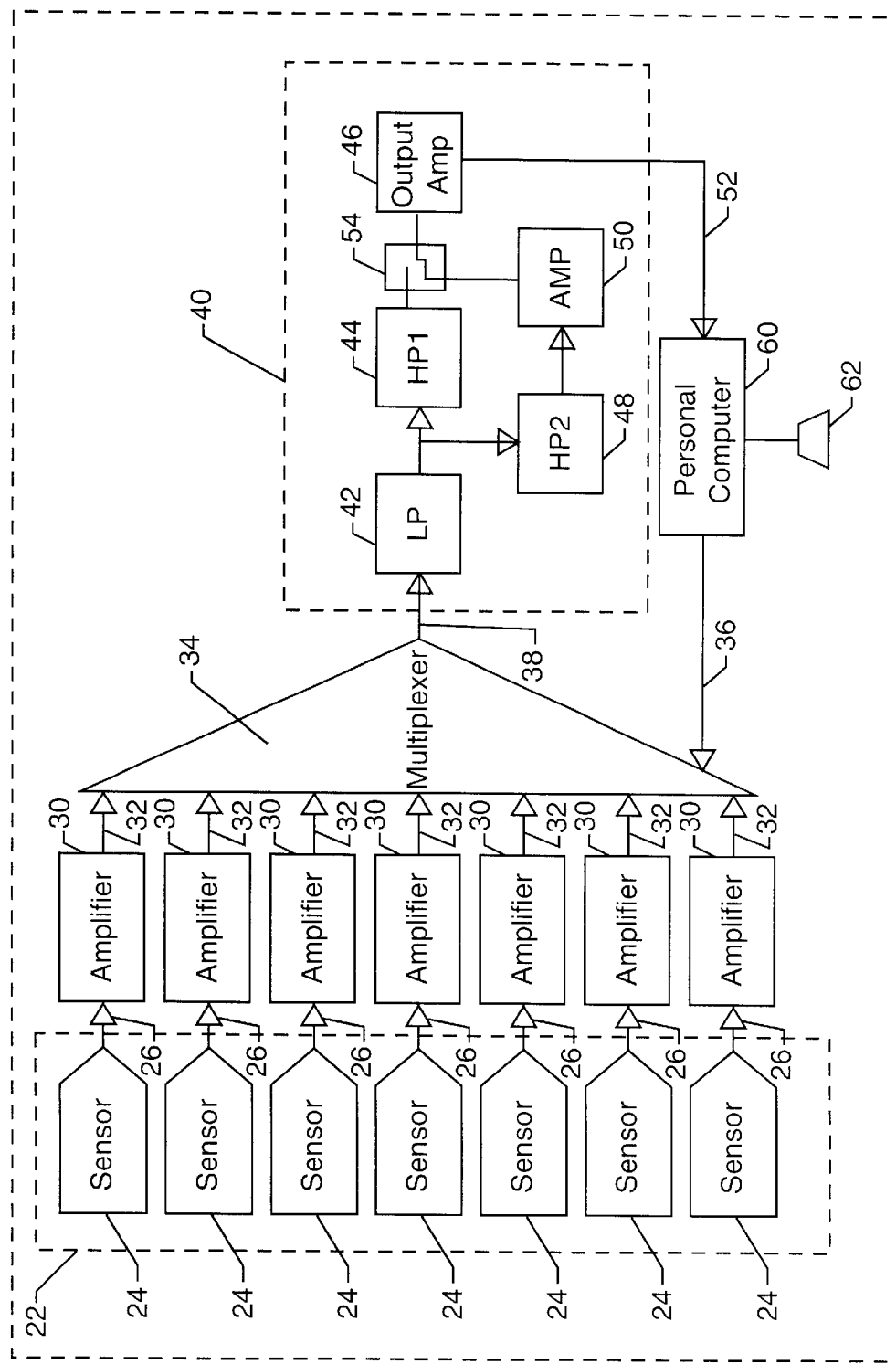
FIG. 5 is a block diagram of the fetal heart monitoring system of the present invention.

Referring to FIG. 5, there is shown a block diagram of a preferred embodiment of a fetal heart monitoring system 20 of the present invention. System 20 generally comprises sensor 22 which is configured to be placed on the abdomen of the expectant mother. In one embodiment, sensor 22 is configured as an ambulatory, non-invasive, passive fetal heart rate monitoring sensor. Sensor 22 comprises a plurality of sensor elements 24 therein to receive the signals emitted by a fetus inside the expectant mother and output a plurality of corresponding signals 26, commensurate with the number of sensor elements 24 inside sensor 22. Such ambulatory, non-invasive, sensor elements are well known in the industry. An example of sensor 22 is described in U.S. Pat. No. 5,140,992 to Zuckerwar et al. entitled "PASSIVE FETAL MONITORING SENSOR."

Referring to FIG. 5, system 20 further includes a plurality of amplifiers 30. Each amplifier 30 has an input for receiving a corresponding sensor signal 26. Amplifiers 30 output corresponding amplified sensor signals 32. In one embodiment, each amplifier 30 includes buffer circuitry, e.g. buffer amplifiers, from which signals 32 are outputted. Commercially available amplifiers can be used to realize amplifiers 30. In one possible embodiment, each amplifier 30 is configured as the commercially available AD 549 amplifier manufactured by Analog Devices. If buffer amplifiers are utilized, each buffer amplifier can be realized by the commercially available LM307 amplifier. Other suitable commercially available components can be used.

Referring to FIG. 5, system 20 further includes multiplexer 34. Multiplexer 34 includes a plurality of inputs for receiving amplified sensor signals 32, and an output for outputting a selected one of the amplified sensor signals 32. Multiplexer 34 further includes an input for receiving control signal 36. Control signal 36 can be a multi-bit digital signal that controls multiplexer 34 to select any one of the sensor signals 32 at any one of the multiplexer inputs and route the selected sensor signal to the output of multiplexer 34 wherein the selected signal is outputted as selected signal 38. The generation of control signal 36 is discussed in the ensuing description.

Referring to FIG. 5, system 20 further comprises signal processing device 40.

Signal processing device 40 includes an input for receiving selected sensor signal 38. Signal processing device 40 generally comprises low pass filter 42, high pass filter 44, amplifier 46, high pass filter 48 and amplifier 50. Low pass filter 42, and high pass filter 44 form a first signal processing channel. Low pass filter 42, high pass filter 48, and amplifier 50 form a second signal processing channel. Signal processing device 40 outputs a signal 52 that was processed either by the first signal processing channel or the second processing channel. Signal processing device 40 further comprises a control device 54 that determines whether selected signal 38 is processed by the first signal processing channel or the second signal processing channel. In one embodiment, control device 54 comprises a switch that can configure signal processing device 40 into a first state wherein selected signal 38 is processed by the first signal processing channel or a second state wherein the selected signal 38 is processed by the second signal processing channel. In one embodiment, control device 54 is manually controlled. In another embodiment, control device 54 is electronically controlled.

Low pass filter 42 is configured as an anti-aliasing filter. In one embodiment, the cutoff-frequency of filter 42 is about 500 Hz. In one embodiment, filter 42 is realized by the commercially available LM 307 amplifier. High pass filter 44 is configured to have a cutoff frequency of about 16 Hz so as to pass spectral content in primary frequency band B (and A) (see FIG. 1).

In accordance with the present invention, control device 54 is configured to effect processing of selected signal 38 with the first signal processing channel (i.e. filters 42 and 44) when the transmission of acoustic fetal heart signals occurs via the direct contact mode. As described in the foregoing discussion, direct contact mode transmission occurs when the back or shoulders of the fetus are in direct contact with maternal abdominal wall 12 as illustrated in FIG. 2. The passband used in this transmission mode, typically 16–50 Hz, contains the bulk of the fetal heart signal energy while blocking signals from the maternal heart tone, typically 8–15 Hz, as well as 60 Hz interference (such as from a power source). The filtered signal outputted by high pass filter 44 passes through control device 54 and is inputted into amplifier 46. Amplifier 46 outputs an amplified processed sensor signal 52. (See discussion below re possible use of monitoring device 60 to help define passband.)

Once fetus 10 moves to the position as illustrated in FIG. 3, signal 52 becomes significantly weak due to amniotic fluid 18. Thus, in accordance with the present invention, control device 54 is configured so as to configure signal processing device 40 into the second state whereby selected sensor signal 38 is processed by the second signal processing channel, i.e. low pass filter 42, high pass filter 48 and amplifier 50. This transmission mode is the fluid propagation mode which was described in the foregoing description. In one embodiment, high-pass filter 48 has a cutoff frequency of about 80 Hz so as to pass spectral content of secondary frequency band B. The output of high-pass filter 48 is inputted into amplifier 50. Amplifier 50 blocks deterministic noise signals and, in one embodiment, has a gain of about 10 so as to preferentially amplify signals in secondary frequency band B.

Thus, as is apparent from the foregoing description, control device 54 enables system 20 to effect signal processing of either direct contact mode sensor signals or fluid propagation mode sensor signals.

Referring to FIG. 5, system 20 further comprises monitoring device 60. Monitoring device 60 can be realized by a microprocessor, personal computer or laptop notebook or any comparable digital instrumentation that is capable of processing fetal heart tone signals outputted by amplifier 46. In order to facilitate understanding of the present invention, the ensuing description is in terms of monitoring device 60 being configured as a personal computer.

Personal computer 60 has a central processing unit and sufficient memory capacity to perform signal processing algorithms such as auto-correlation, Fourier Transforms, Discrete Fourier Transforms and adaptive filtering processes. Personal computer 60 is also configured for performing an algorithm that determines the figure of merit for processed signal 52. Such an algorithm is described in commonly owned U.S. Pat. No. 5,524,631, the disclosure of which is incorporated herein by reference as if set forth in its entirety.

Personal computer 60 includes an input for receiving processed sensor signal 52, a sound interface card, an analog-to-digital converter ("ADC"), and an audio speaker 62. Personal computer 60 further includes user interface devices such as a keyboard and mouse (not shown). Personal computer 60 is programmed with the appropriate software to realize a filter, such as an elliptical filter having an adjustable center frequency. The elliptical filter provides filtering in addition to filters 42, 44 and 48. In a preferred embodiment, the elliptical filter is an eight-pole elliptical band pass filter. For example, in one embodiment, the elliptical filter provides a lower cutoff frequency of 16 Hz, which is the same as the cutoff frequency of high pass filter 48, and an upper cutoff frequency of about 50 Hz. In this example, the pass band is between 16 Hz and 50 Hz. However, since the elliptical filter is programmable and the center frequency is adjustable, the user can use the keyboard to accurately and quickly change the characteristics of the elliptical filter. For example, the elliptical filter can be configured to have passbands of 80–110 Hz, 110–170 Hz, 190–290 Hz and 310–450 Hz. These passbands block line power frequencies of 60 Hz and odd harmonics 180 Hz and 300 Hz (the even harmonics 120 and 240 Hz cause no interference). Thus, the user can select the passband that provides the signal having the best figure of merit. The signal having the best figure of merit can be stored, visually displayed on a monitor and/or presented via audio speaker 62.

In a preferred embodiment, the ADC of personal computer 60 samples at a rate of 2 kHz. Therefore, low pass filter 42 is configured to filter out all frequencies in signal 38 that are above 1 kHz.

In a preferred embodiment, personal computer 60 is also used to determine which of the sensor elements 24 is outputting the signal having the best figure of merit. Personal computer 60 is programmed to select a particular one of the amplified sensor signals 32 inputted into multiplexer 34 as a default sensor signal. Accordingly, personal computer 60 generates control signal 36 that selects the multiplexer input having the default sensor signal. The default sensor signal is passed through multiplexer 34 and signal processing device 40. The figure of merit is then determined for that particular selected signal. This process is then repeated for all amplified signals 32 in order to determine which of the amplified signals 32 has the best figure of merit. In one embodiment, this process is accomplished by the user using the keyboard to manually input data corresponding to each amplified signal 32 so as to generate the appropriate control signals 36. In another embodiment, personal computer 60 is configured to automatically determine and compare the figures of merit for amplified signals 32 at predetermined time intervals. As explained above, the signal having the best figure of merit can be, for example, stored, visually displayed on a monitor and/or presented via audio speaker 62.

During a particular mode of operation, e.g. direct contact mode, if all the figures of merit for all amplified signals 32 fall below predetermined criteria, then it is apparent that fetus 10 has moved to another position and that control device 54 must be manipulated to effect signal processing that corresponds to the other mode of operation, e.g. fluid propagation mode.

Figure 4:
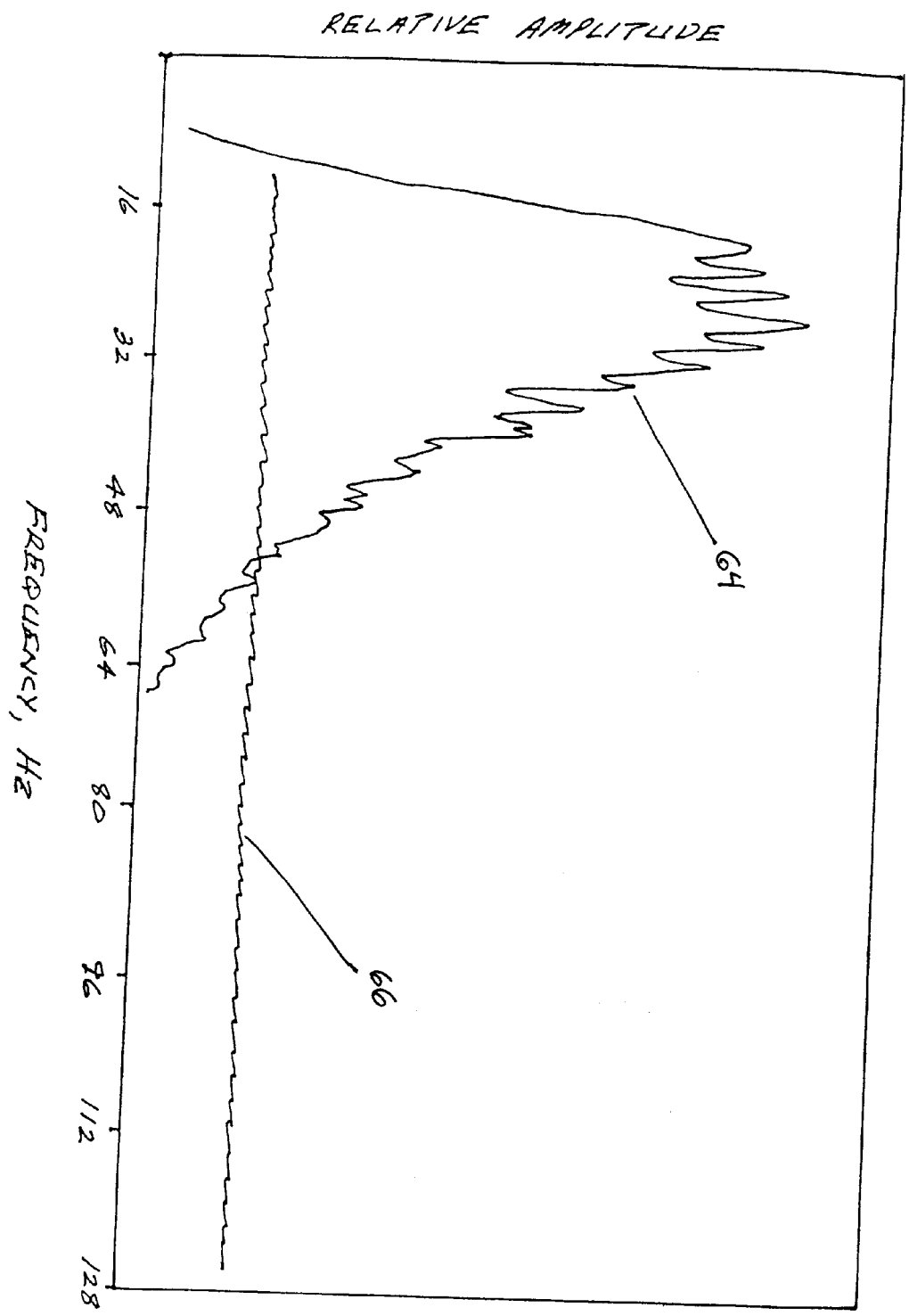
FIG. 4 illustrates a typical background noise spectrum associated with the frequency spectrum of detected fetal heart sounds.
Figure 4:
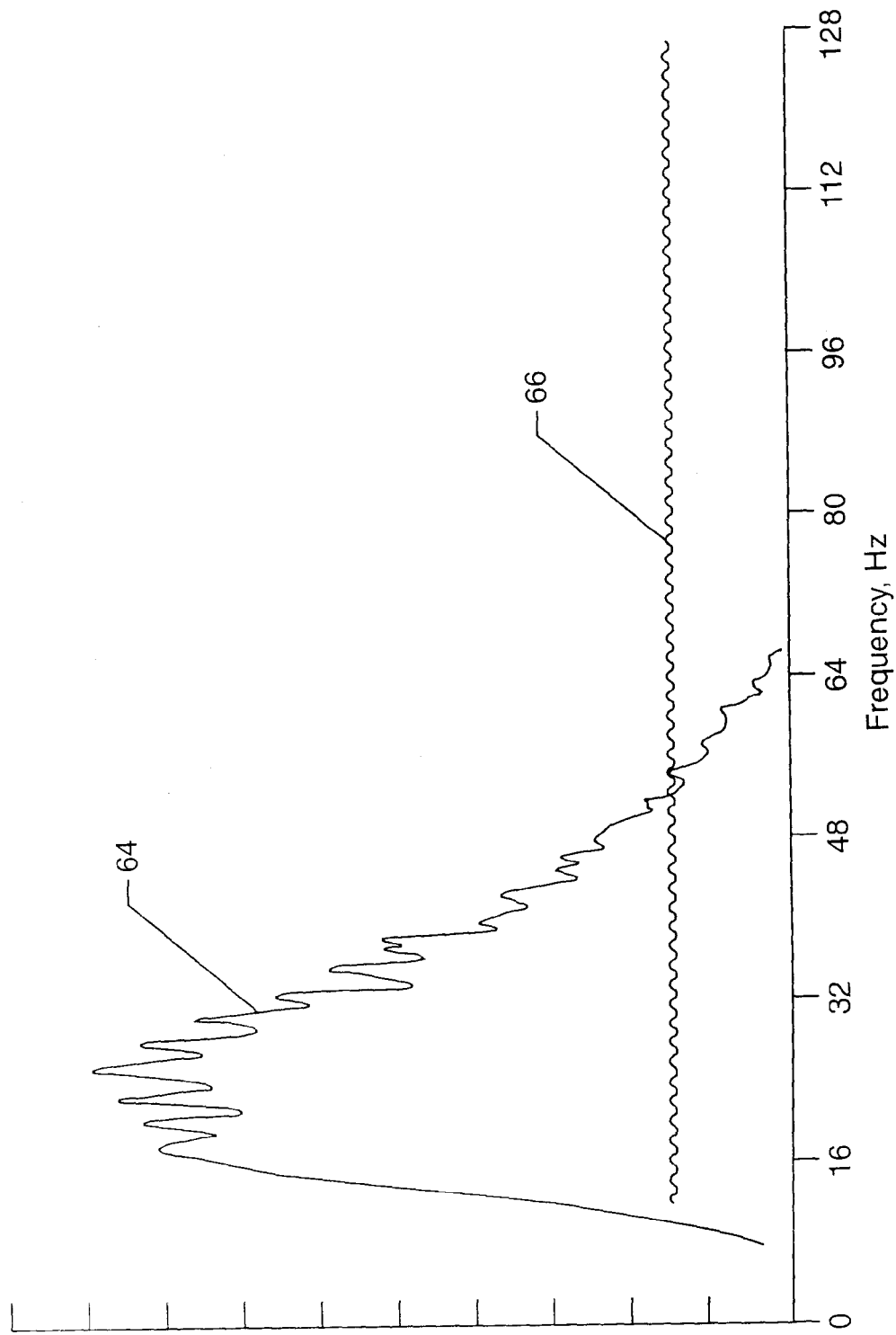

Referring to FIG. 1, the signals in secondary frequency band B are typically 30 dB down relative to the signals in the primary frequency band A. The limiting factor in the detection of low-level signals is background noise. A typical background noise spectrum is shown in FIG. 4. The background noise has two components: (i) a deterministic component 64 attributed to maternal fluid-generated sounds, heart beat, souffle and non-maternal sounds generated by building vibrations and low-frequency airborne sounds, all of which are prominent in primary frequency band A, and (ii) a random component 66 that is attributed mainly to electronic Johnson noise which is uniform over the entire frequency spectrum. It has been found that substantially eliminating noise component 64 while taking advantage of the increased signal power of signals in the secondary frequency band B achieves a significant improvement in the signal-to-noise ratio of signals in secondary frequency band B which more than compensates for the 30 dB loss of signal strength occurring when shifting the signal detection process to the secondary frequency band B. Filters 42, 44 and 48 in conjunction with the signal processing techniques, e.g. averaging, autocorrelation and adaptive filtering, implemented by personal computer 60 substantially eliminate the aforementioned noise components thereby improving the signal-to-noise ratio of signals in the secondary frequency band B so as to enable accurate and reliable detection of signals in secondary frequency band B.

Thus, system 20 of the present invention solves the problems associated with the conventional fetal heart monitoring systems. In particular, the utilization of the fluid propagation mode expands the detectable surface area of the fetal heart signals on the maternal abdominal wall and dispenses with the need for multiple sensors.

In at least one embodiment, the present invention can be embodied in the form of computer processor readable program code embodied in a computer processor usable medium, such as floppy diskettes, CD-ROMs, hard drives, or any other computer-readable storage medium, wherein, when the computer program code is loaded into and executed by a computer, the computer becomes an integral part of an apparatus for practicing the invention.

An example of a fetal heart monitoring sensor with which the present invention might be utilized can be found in U.S. patent application Ser. No. 09/784,414 filed contemporaneously with the instant application on Feb. 13, 2001, entitled "Passive Fetal Heart Monitoring System and Method For Simultaneously Making a Plurality of Acoustic Signal Sensor Elements" with inventors: T. Bryant, M. Wynkoop, N. Holloway and A. Zuckerwar, and which is identified by Attorney Docket No. LAR-15602-1. This patent application is hereby incorporated by reference as if set forth in its entirety herein.

The principals, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations in changes may be made by those skilled in the art without departing from the spirit of the invention. Accordingly, the foregoing detailed description should be considered exemplary in nature and not limited to the scope and spirit of the invention as set forth in the attached claims.

Thus, having described the invention, what is claimed is:

1. A fetal heart monitoring system, comprising:
   a passive fetal heart monitoring sensor having a plurality of sensor elements for acquiring acoustic signals emitted from a fetus inside a body and outputting a plurality of sensor signals;
   a selection circuit for selecting a particular one of the sensor signals;
   a signal processing device having a first signal processing channel for processing acoustic signals in a first frequency band and a second signal processing channel for processing acoustic signals in a second frequency band, the signal processing device having a first state such that the signal processing device outputs sensor signals processed by the first signal processing channel and a second state such that the signal processing device outputs sensor signals processed by the second signal processing channel;
   a monitoring device responsive to the signal processing device for monitoring the characteristics of the processed signals outputted by the signal processing device and determining if such characteristics meet or exceed predetermined criteria; and
   a control device for configuring the signal processing device to the first state so as to process selected sensor signals with the first signal processing channel if such processed signals meet or exceed the predetermined criterion and for configuring the signal processing device to the second state so as to process selected sensor signals with the second signal processing channel if the sensor signals processed by the first signal processing channel do not meet the predetermined criteria.

2. The fetal heart monitoring system according to claim 1 wherein the control device configures the signal processing device back to the first state so as to process selected sensor signals with the first signal processing channel if the signals processed by the second signal processing channel do not meet predetermined criteria.

3. The fetal heart monitoring system according to claim 1 wherein the selection circuit comprises a multiplexer having a plurality of inputs and an output, each input being connected to a corresponding sensor output signal, the multiplexer further including an input for receiving a control signal that configures the multiplexer so as to couple any one of the multiplexer inputs to the multiplexer output.

4. The fetal heart monitoring system according to claim 3 wherein the monitoring device includes means for generating the control signal for input to the multiplexer.

5. The fetal heart monitoring system according to claim 1 further comprising an amplifier for amplifying the signals outputted by the sensors.

6. The fetal heart monitoring system according to claim 1 wherein the signal processing device further comprises an amplifier for amplifying the processed sensor signals outputted by the first and second signal processing channels.

7. The fetal heart monitoring system according to claim 1 wherein the monitoring device includes a microprocessor programmed to perform signal processing algorithms on the processed sensor signal outputted by the signal processing device.

8. The fetal heart monitoring system according to claim 1 wherein the monitoring device includes circuitry for generating audio signals representative of the acoustic signals emanating from the heart of the fetus.

9. The fetal heart monitoring system according to claim 1 wherein the monitoring device comprises an additional signal processing device for further processing said outputted sensor signals.

10. A fetal heart monitoring system, comprising:
 a passive fetal heart monitoring sensor having a plurality of sensor elements for acquiring acoustic signals emitted from a fetus inside a body and outputting a plurality of sensor signals;
 a selection circuit for selecting a particular one of the sensor signals;
 a signal processing device having a first signal processing channel for processing acoustic signals in a first frequency band and a second signal processing channel for processing acoustic signals in a second frequency band, the signal processing device having a first state such that the signal processing device outputs sensor signals processed by the first signal processing channel and a second state such that the signal processing device outputs sensor signals processed by the second signal processing channel;
 a monitoring device responsive to the signal processing device for monitoring the characteristics of the processed signals outputted by the signal processing device and determining if such characteristics meet or exceed predetermined criteria; and
 a control device for configuring the signal processing device to the first state so as to process selected sensor signals with the first signal processing channel if such processed signals meet or exceed the predetermined criterion and for configuring the signal processing device to the second state so as to process selected sensor signals with the second signal processing channel if the sensor signals processed by the first signal processing channel do not meet the predetermined criteria, wherein the control device comprises a switch.

11. The fetal heart monitoring system according to claim 10 wherein the switch is configured as a manually operated switch.

12. The fetal heart monitoring system according to claim 10 wherein the control device configures the signal processing device back to the first state so as to process selected sensor signals with the first signal processing channel if the signals processed by the second signal processing channel do not meet predetermined criteria.

13. The fetal heart monitoring system according to claim 10 wherein the selection circuit comprises a multiplexer having a plurality of inputs and an output, each input being connected to a corresponding sensor output signal, the multiplexer further including an input for receiving a control signal that configures the multiplexer so as to couple any one of the multiplexer inputs to the multiplexer output.

14. The fetal heart monitoring system according to claim 10 further comprising an amplifier for amplifying the signals outputted by the sensors.

15. The fetal heart monitoring system according to claim 13 wherein the monitoring device includes means for generating the control signal for input to the multiplexer.

16. The fetal heart monitoring system according to claim 10 wherein the signal processing device further comprises an amplifier for amplifying the processed sensor signals outputted by the first and second signal processing channels.

17. The fetal heart monitoring system according to claim 10 wherein the monitoring device includes a microprocessor programmed to perform signal processing algorithms on the processed sensor signal outputted by the signal processing device.

18. The fetal heart monitoring system according to claim 10 wherein the monitoring device includes circuitry for generating audio signals representative of the acoustic signals emanating from the heart of the fetus.

19. A fetal heart monitoring system, comprising:
 a passive fetal heart monitoring sensor having a plurality of sensor elements for acquiring acoustic signals emitted from a fetus inside a body and outputting a plurality of sensor signals;
 a selection circuit for selecting a particular one of the sensor signals;
 a signal processing device having a first signal processing channel for processing acoustic signals in a first frequency band and a second signal processing channel for processing acoustic signals in a second frequency band, the signal processing device having a first state such that the signal processing device outputs sensor signals processed by the first signal processing channel and a second state such that the signal processing device outputs sensor signals processed by the second signal processing channel;
 a monitoring device responsive to the signal processing device for monitoring the characteristics of the processed signals outputted by the signal processing device and determining if such characteristics meet or exceed predetermined criteria;
 a control device for configuring the signal processing device to the first state so as to process selected sensor signals with the first signal processing channel if such processed signals meet or exceed the predetermined criterion and for configuring the signal processing device to the second state so as to process selected sensor signals with the second signal processing channel if the sensor signals processed by the first signal processing channel do not meet the predetermined criteria; and
 wherein the first signal processing channel comprises a low pass anti-aliasing filter for filtering signals outputted by the selection circuit, and a high pass filter configured to pass only signals having frequencies in the first frequency band.

20. A fetal heart monitoring system, comprising:
a passive fetal heart monitoring sensor having a plurality of sensor elements for acquiring acoustic signals emitted from a fetus inside a body and outputting a plurality of sensor signals;
a selection circuit for selecting a particular one of the sensor signals;
a signal processing device having a first signal processing channel for processing acoustic signals in a first frequency band and a second signal processing channel for processing acoustic signals in a second frequency band, the signal processing device having a first state such that the signal processing device outputs sensor signals processed by the first signal processing channel and a second state such that the signal processing device outputs sensor signals processed by the second signal processing channel;
a monitoring device responsive to the signal processing device for monitoring the characteristics of the processed signals outputted by the signal processing device and determining if such characteristics meet or exceed predetermined criteria; and
a control device for configuring the signal processing device to the first state so as to process selected sensor signals with the first signal processing channel if such processed signals meet or exceed the predetermined criterion and for configuring the signal processing device to the second state so as to process selected sensor signals with the second signal processing channel if the sensor signals processed by the first signal processing channel do not meet the predetermined criteria; and
wherein the second signal processing channel comprises a low pass anti-aliasing filter for filtering signals outputted by the selection circuit, and a high pass filter configured to pass only signals having frequencies in the second frequency band.

21. The fetal heart monitoring system according to claim 20 wherein the second signal processing channel further comprises an amplifier for amplifying signals outputted by the high pass filter.

22. An article of manufacture comprising:
a computer processor usable medium having computer processor readable program code embodied therein for monitoring cardiac activity of a fetal heart using a fetal heart monitoring system comprising a passive fetal heart monitoring sensor having a plurality of sensor elements for acquiring acoustic signals emitted from a fetus inside a body and outputting a plurality of sensor signals, a selection circuit for selecting a particular one of the sensor signals, a signal processing device having a first signal processing channel for processing acoustic signals in a first frequency band and a second signal processing channel for processing acoustic signals in a second frequency band, the signal processing device having a first state such that the signal processing device outputs sensor signals processed by the first signal processing channel and a second state such that the signal processing device outputs sensor signals processed by the second signal processing channel, a monitoring device responsive to the signal processing device for monitoring the characteristics of the processed signals outputted by the signal processing device and determining if such characteristics meet predetermined criteria, and a control device for configuring the signal processing device in either the first state or the second state, the computer processor readable program code in the article of manufacture comprising:
computer processor readable program code configured to cause the system to select a particular one of the sensor signals;
computer processor readable program code configured to cause the system to monitor the characteristics of the processed signals outputted by the signal processing device to determine if the processed sensor signal meets predetermined criteria; and
computer processor readable program code configured to cause the system to configure the signal processing device in the first state such that first signal processing channel processes the sensor signals when such processed sensor signals meet predetermined criteria and to configure the signal processing device in the second state such that the sensor signals are processed by the second signal processing channel when the processed sensor signals outputted by the first signal processing channel do not meet predetermined criteria.

23. The article of manufacture according to claim 22 further comprising computer processor readable program code configured to cause the system to configure the signal processing device back to the first state when the sensor signals processed by the second signal processing channel do not meet predetermined criteria.

24. The article of manufacture according to claim 22 wherein the monitoring device further comprises an additional signal processing device.

25. A method of monitoring fetal heart activity, comprising the steps of:
providing a fetal heart monitoring system comprising a passive fetal heart monitoring sensor having a plurality of sensor elements for acquiring acoustic signals emitted from a fetus inside a body and outputting a plurality of sensor signals, and a signal processing device having a first signal processing channel for processing acoustic signals in a first frequency band and a second signal processing channel for processing acoustic signals in a second frequency band, the signal processing device having a first state such that the signal processing device processes sensor signals with the first signal processing channel when such processed signals meet predetermined criteria and a second state such that the sensor signals are processed by the second signal processing channel when the processed signals outputted by the first signal processing channel do not meet predetermined criteria;
processing the sensor signals with one of the signal processing channels of the signal processing device;
monitoring the characteristics of the processed sensor signals to determine if such processed sensor signals meet predetermined criteria; and
configuring the signal processing device so as to process the sensor signals with the other signal processing channel if the processed signals do not meet predetermined criteria.

26. The method according to claim 25 further comprising the step of amplifying the sensor signals.

27. The method according to claim 25 further comprising the step of amplifying the processed signals outputted by the first and second signal processing channels.

28. The method according to claim 27 wherein said step of monitoring the characteristics of the processed sensor signals further comprises filtering of the amplified processed sensor signals.

29. The method according to claim 25 wherein the processing step comprises the steps of:

configuring the signal processing device in the first state;

filtering the selected sensor signals with a low pass anti-aliasing filter; and filtering the previously filtered selected sensor signals with a high pass filter configured to pass only signals having frequencies in the first frequency band.

30. The method according to claim 25 wherein when the processing step comprises the steps of:

configuring the signal processing device in the second state;

filtering the selected sensor signals with a low pass anti-aliasing filter;

filtering the previously filtered selected sensor signals with a high pass filter configured to pass only signals having frequencies in the second frequency band; and thereafter, amplifying the filtered signals.

31. The method according to claim 25 further comprising the step of generating audio signals representative of the acoustic signals emanating from the heart of the fetus.

\* \* \* \* \*

UNITED STATES PATENT AND TRADEMARK OFFICE
CERTIFICATE OF CORRECTION

PATENT NO. : 6,551,251 B2
DATED : April 22, 2003
INVENTOR(S) : Allan J. Zuckerwar et al.

It is certified that error appears in the above-identified patent and that said Letters Patent is hereby corrected as shown below:

Drawings,
Delete Figure 4 and substitute therefor Figure 4 as shown on the attached page.

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,551,251 B2
DATED        : April 22, 2003
INVENTOR(S)  : Allan J. Zuckerwar et al.

It is certified that error appears in the above-identified patent and that said Letters Patent is hereby corrected as shown below:

Drawings,
Delete Figure 4 and substitute therefor Figure 4 as shown on the attached page.

This certificate supersedes Certificate of Correction issued September 16, 2003.

Signed and Sealed this

Fourteenth Day of October, 2003

JAMES E. ROGAN
*Director of the United States Patent and Trademark Office*